United States Patent [19]
Lindhofer et al.

[11] Patent Number: 5,945,311
[45] Date of Patent: *Aug. 31, 1999

[54] METHOD FOR PRODUCING HETEROLOGOUS BI-SPECIFIC ANTIBODIES

[75] Inventors: Horst Lindhofer, München; Stephan Thierfelder, Eichenau, both of Germany

[73] Assignee: GSF—Forschungszentrumfür Umweltund Gesundheit, Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/758,430

[22] Filed: Nov. 29, 1996

Related U.S. Application Data

[63] Continuation-in-part of application No. PCT/EP95/01850, May 16, 1995.

[30] Foreign Application Priority Data

Jun. 3, 1994 [DE] Germany ............................... 44 19 399

[51] Int. Cl.⁶ ..................................................... C12P 21/04
[52] U.S. Cl. .................... 435/70.21; 435/70.2; 435/328; 530/387.3; 530/388.1
[58] Field of Search ............................... 435/70.2, 70.21, 435/328; 530/387.3, 388.1

[56] References Cited

FOREIGN PATENT DOCUMENTS 2 197 322   5/1988   United Kingdom .
2 197 323   5/1988   United Kingdom .

OTHER PUBLICATIONS

Bjorck et al., J. of Immunology, vol. 133: 969–974, 1984, Aug., 1984.
Lindhofer et al. J. Immunology vol. 155: 219–225, 1995.
S. Ferrini et al, "Targeting of T–Lymphocytes Against EGF–Receptor⁺ Tumor Cells by Bispecific Monoclonal Antibodies: Requirement of CE3 Molecule Cross–Linking For T–Cell Activation.", *International Journal of Cancer*, vol. 55, No. 6, Dec. 2 1993, pp. 931–937.
V. Lebegue et al., "Producti Onet Caracterisation D,Anticorps Monoclonaux Hybrides Presentant Une Double Isotyple IgG1/IgG3.", *Comptes Rendus de l'Academie des Sciences*, vol. 310, No. 9, Apr. 26, 1990, Paris, pp. 377–382.
M.Clark et al., "T–Cell Killing of Target Cells Induced by Hybrid Antibodies: Comparison of Two Bispecific Monoclonal Antibodies.", *Journal of the National Cancer Institute*, vol. 79, No.6, 12/87, MD, pp. 1393–1401.

Primary Examiner—Christina Y. Chan
Assistant Examiner—Patrick J. Nolan
Attorney, Agent, or Firm—Klaus J. Bach

[57] ABSTRACT

In a method for producing heterologous bi-specific antibodies, a quadroma is provided which is fused from hybridromas one of which generates antibodies that have an affinity to the binding site of protein A and another of which generates antibodies that have a weaker or no affinity to the binding domain of protein A, by multiplying and cultivating the quadromas and by eluting the bi-specific antibodies in a pH range at least 0.5 units above the pH value at which the antibodies with greater affinity to the binding domain of protein A are still bonded.

8 Claims, 4 Drawing Sheets

METHOD FOR PRODUCING HETEROLOGOUS BI-SPECIFIC ANTIBODIES

BACKGROUND OF THE INVENTION

This is a Continuation-in-Part application of International application PCT/EP95/01850 filed May 16, 1995 and claiming the priority of German application P 44 19 399.8 filed Jun. 3, 1994.

The invention relates to a method of producing heterologous bi-specific antibodies with a high level of purity.

Definition of some of the terms used in this specification:

Bi-specific antibodies (bsab): A bi-specific antibody comprises pairs consisting of a heavier and a lighter immune globulin chain, homologous to a monoclonal antibody of which one is directed against a particular antigen whereas the other heavy/light immune globulin chain pair is homologous to a monoclonal antibody which recognizes an other antigen. This results in a capability for the bi-specific antibody to simultaneously bind two different antigens.

Heterologous bi-specific antibodies: In this connection such bi-specific antibodies are called heterologous which include heavy/light immunoglobulin chain pairs of different species or subclasses.

Quadroma=hybrid–hybridoma: Quadromas result from the fusion of two antibody-producing hybridoma cells.

Parental antibodies: Parental antibodies are also produced by quadromas. They are identical with the monoclonal antibodies of the original clones which are used for making the quadromas (see FIG. 1).

Bi-specific antibodies (bsab) have a multitude of application areas including immune diagnostics [1], therapies (for example, immune therapy of tumors [2], suppression of rejection- and auto-immune reactions [3]) in humans. In principle, bi-specific antibodies can be provided by three different methods, that is, by chemical conjugation [4], by gene-technological methods [5] or by fusion of two hybridoma cell lines [6]. Bi-specific antibodies which are made using the last-mentioned method have the advantage to be "real" antibodies with a correct glycosylation which can be derived in a reproducible manner from a clearly defined clone. However, it is an essential disadvantage of this method that the culture supernatants of such hybrid-hybridomas contain up to 10 different antibody molecules which develop by the free combination of heavy and light immunoglobulin chains. For this reason, relatively complicated purification procedures for the isolation of the correctly paired bi-specific antibodies are necessary.

There is a number of purification procedures for bi-specific antibodies, almost all of which use common chromatographic methods such as cation and anion exchanger chromatography, hydroxylapatite and affinity chromatography. A common feature of all these methods is that optimal purity grades can be achieved only after implication of at least two different separating mechanisms (column passages). This is a substantial disadvantage for a large scale industrial purification procedure. A method which is used more frequently lately and which tries to circumvent this disadvantage is therefore discussed: This is the cation exchanger chromatography (CA) which is based on the different charges of different immunoglobulins at a given acid pH value (usually between pH 4.5–5.8). It permits, under certain conditions, to isolate the bi-specific antibody fractions in a single purification step.

Although the single-step purification is advantageous there are some important disadvantages particularly in connection with large-scale industrial purification of bi-specific antibodies:

a) To a cation exchanger column not only immunoglobulin are attached but also all other proteins which are positively charged at the given pH value (such as bovine serum albumin and also bovine immunoglobulin) as it is known from [8], b) at the same time, the capacity of the column for bi-specific antibodies is reduced, c) because the possibility for combinations between the heavy and light chains in mouse/mouse or respectively rat/rat quadroma is generally not limited [7], there are up to 10 antibody variations. Cation exchanger columns can separate such variations up to a certain degree as they have different charges [8]. In principle however, this is possible only with bi-specific antibodies in which the parental monoclonal antibodies have light and heavy Ig-chains with sufficiently different charges in the particular buffer system that is used for the redemption. That means that, for certain bi-specific antibodies with disadvantageous antibody combinations, a separation or purification by way of cation exchanger chromatography is not possible.

d) the separation material is expensive, e) with anteceding concentrating procedures such as salt precipitation, the bi-specific antibodies may be partially denaturalized.

It is further known from Ey et al. [9] that, at different pH values, subclasses of the mouse can be eluted from protein A. Also tests have already been made to utilize this property of protein A for the purification of the bi-specific antibodiy fraction of mouse/mouse quadromas. The most essential disadvantages of the above methods are as follows:

1. With the cleaning methods described so far [10, 11], first all secerned antibody variations are attached to protein A. Therefore one third less capacity is available for the binding of the bi-specific antibodies to the protein A column than with the method described herein.

2. As a result of the binding of all the antibody variations which have been secerned from a mouse/mouse quadroma, the separation of the undesirable parental antibodies from the bi-specific antibody fraction to be purified using the sequential pH elution is not very precise.

3. An essential factor in the production and the purification of bi-specific antibodies is the control of the mismatches of heavy and light Ig-chains. With mouse/mouse or respectively, rat/rat bi-specific antibodiy combinations, this may be an unsolvable problem.

It is the object of the present invention to provide a method of this type with which however it is possible to produce bi-specific antibodies of high purity.

SUMMARY OF THE INVENTION

In a method for producing heterologous bi-specific antibodies, a quadroma is provided by fusion from hybridromas one of which generates antibodies that have an affinity to the binding domain of protein A and another of which generates antibodies that have a weaker or no affinity to the binding domain of protein A, by multiplying and cultivating the quadromas and by eluting the bi-specific antibodies in a pH range at least 0.5 units above the pH value at which the antibodies with greater affinity to the binding domain of protein A are still bonded.

When compared to the methods described in the introductory part, the method according to the invention has the following advantages:

with the heterologous bi-specific antibody combinations proposed herewith, detection, particularly of the two light chains for which there are subclass differences is facilitated which provides for a substantially improved quality control for the bi-specific antibodies.

Only the present inventors have found that in mouse/rat quadromas, there is a higher bi-specific antibody yield made possible by a preferred correct heavy/light Ig chain match up.

Since, with the method according to the invention, one of the parental antibodies which is part of the bi-specific antibodies will generally not attach to a protein A, the discrimination of the bi-specific antibody fraction from the second parental antibody fraction which attaches to protein A is substantially improved. With this discovery, the improved utilization of the possibility of purifying heterologous bi-specific antibodies via protein A obtains a whole new dimension when compared to mouse/mouse or rat/rat bi-specific antibodies. Because of the much reduced portion of mismatches (reduced from 70% to 10–30% depending on the clone combinations, see FIG. 1) of heavy and light Ig chains, an enormous amount of energy and costs (electricity for incubators, growth media, etc.,) and capacity of the protein A column are saved.

The invention is based, in principle, on the different affinity constants of a homologous —($CH_2$—$CH_3$)2 immunoglobulin region and a heterologous —($CH_2$—$CH_3$) ($CH_2'$—$CH_3'$) immunoglobulin region versa protein A. In this case, with the hetero-($CH_2$—$CH_3$) configuration only one $CH_2$—$CH_3$ region contributes to the attachment to a protein A. The second ($CH_2'$—$CH_3'$)—region may, after completed attachment of the bi-specific antibodies to protein A, reinforce that attachment under certain circumstances. The different affinity constants of the immunoglobulins with homo- and hetero-configurations with regard to protein A are utilized for the purification of the bi-specific components.

An important point of this new purification principle for bi-specific antibodies is that one of the parental antibodies, which are also secerned from the quadroma cells, does not form a bond with a protein A. That means that one of the hybridoma cell lines which is fused with a second hybridroma cell line to a quadroma should produce an antibody which does not form a bond with a protein A. As a result of this condition, there is a relatively large difference between the affinity constants of the bi-specific antibodies and the second parental antibody (which should bond well with protein A) with respect to protein A which is important for a good separation of these two antibody variants. This important condition is obtained most efficiently by fusion of a cell line which produces mouse antibodies with a cell line that produces rat antibodies. However, the rat antibody subclass Ig G 2c is excepted from this rule since it is the only one of the rat antibodies which has a sufficiently high affinity to protein A.

Another combination by which these conditions are fulfilled is the combination of the human subclass IgG3 (which establishes no bonds to protein A) with one of the human subclasses IgG1, IgG2a and IgG2b.

Another point which is important for a simple purification of bi-specific antibodies is an obviously preferential pairing of the heavy and the light immunoglobulin chains within a species to form quadroma cells. That means that a quadroma which was formed by the fusion of a rat hybridoma with a mouse hybridoma pairs the light Ig-chain of the mouse mostly with the heavy Ig-chain of the mouse and, in an analog manner, the light Ig chain of the rat pairs up mostly with the heavy Ig chain of the rat. The pairing of the heavy chains on the other hand is apparently not restringed. A number of tests wherein the free combination capability of heavy and light chains within mouse/mouse quadromas was examined led to the conclusion that there is generally no restriction with regard to a free combination capability between two heavy and two light Ig chains respectively [7]. That means if the sum of all the antibody variants secerned from a mouse/mouse quadroma is taken as being 100% the percentage of the correctly paired bi-specific components is between 7.5 and 10% [7,8].

However, in the heterologous mouse/rat quadromas tested by the inventors the portion of the correctly paired bi-specific antibodies increased three-fold to 20–30%. A higher portion cannot be obtained because of the obviously continuing free combinations of the heavy chains with one another.

In summary, the manufacture of heterologous bi-specific antibodies with subsequent purification by way of protein A has the following advantages:

a) an up to three-fold increase in the portion of correctly paired bi-specific antibodies when compared with conventional mouse/mouse or rat/rat quadromas, b) if one of the parental origin antibodies is in the human subclass IgG3 (or the $CH_2$—$CH_3$ region thereof) even bsab humanized antibodies can be isolated. In this case, the correct pairing of the rat- and mouse Fab domain could still be utilized as explained more clearly in example 2, c) bi-specific antibodies which are based on parental origin antibodies with very similar isoelectrical points and which, consequently, cannot be distinguished by way of cation exchanger chromatography, can be isolated, d) it permits a simple one-step purification of the bi-specific antibody components by way of protein A under particularly gentle conditions wherein only very little or no denaturalization of the bi-specific antibodies occurs (elution at pH 5.6–6.0; 100 mM Na Citrate). As a result, the bi-specific antibodies obtained have a new quality, e) there is no contamination by bovine immunoglobulins (in contrast to cation exchangers) since those bond with protein A only at a pH value >7 under high-salt conditions (>1M NaCl), f) no contamination occurs by other proteins contained in the serum (in contrast to the cation exchanger) since those proteins have generally no affinity to protein A, g) in comparison with the other chromatographic separation media protein A is the least expensive separation medium by a wide margin;

h) protein A has excellent separation properties already at low pressures so that no expensive HPLC technique is needed; rather a FPLC technique which, for large scale use is much more advantageous can be used, i) the rate of mismatches of the heavy and light Ig chains with rat/mouse quadromas can be determined by species-specific antiserums.

The sum of all these improvements compensates for the earlier mentioned disadvantage of the quadroma technology which has a relatively low yield of bi-specific antibodies so that the advantages are clearly prevalent. The method proposed herein may well contribute in providing the enormous quantities of bi-specific antibodies at reasonable costs which would be required for an acceptance of the bi-specific antibody therapy in hospitals.

Protein A is a cell wall component of staphylococcus aureus and binds to the Fc region of immunoglobulin of a number of species and subclasses of different affinities. It is a polypeptide chain of 42 KDa size and contains five domains. Four highly homologous domains, of which each one corresponds to a monovalent Fc-binding domain, are arranged in a sequence. By means of Trypsinverdau active fragments can be isolated which correspond to these homologous domains and have a size of 7 KDa. The fragments bind to the FMC part of immunoglobulin in a stoichiometric relation of 2:1. From crystallographic data Deisenhofer [9] was able to derive that such a protein A fragment binds at a location between the $CH_2$ and $CH_3$ region with cooperation of same amino acid rests of a C-proximal projection of the $CH_2$ region.

In summary, it can be said that apparently two immunoglobulins bond with a protein A molecule wherein four homologous domains of the protein A molecule participate. It is therefore possible to use as column material fragments of protein A which contains at least two contiguous fragments B (binding domains).

The invention will be described below on the basis of a number of examples and the accompanying drawings.

DESCRIPTION OF VARIOUS EXAMPLES

The first bi-specific antibody is produced by a quadroma which was generated by the fusion of two hybridoma cells of different species.

The original clones produce 1) an anti-mouse-CD3 rat antibody of the subclass IgG2b and 2) an antimouse-Thy-1.2 mouse antibody of the subclass IgG2a.

Figure 2:
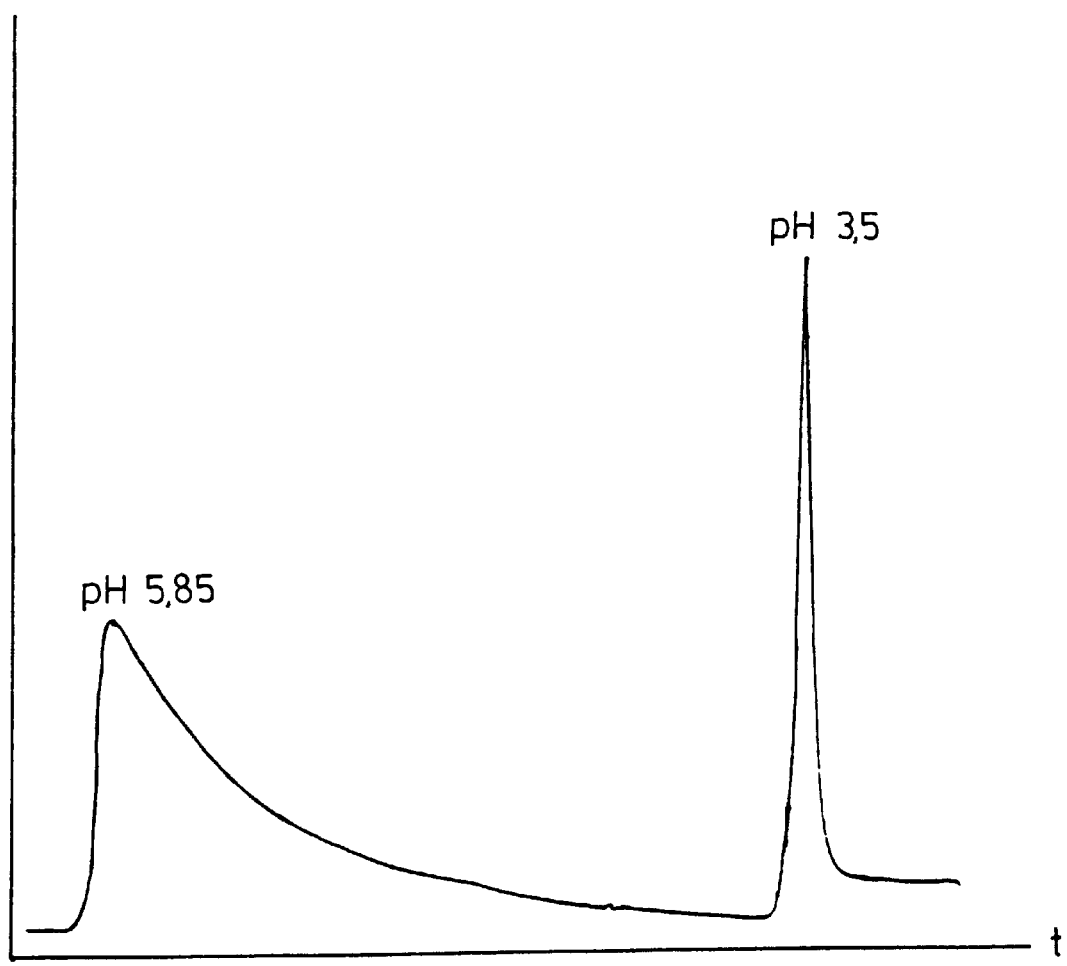
FIG. 2 shows the purification process by way of protein A.

One liter of culture supernatant of the bi-specific antibodies was adjusted to a pH 7 and was sterile-filtered with a 0.2 mm filter. The so-treated culture supernatant was conducted overnight through a 5 ml protein A column and nonbonded serum components and the non-binding parental rat antibodies and homo Fc variants were subsequently removed with 10 column volumes PBS. With a 0.1M Na-citrate buffer adjusted to a pH 5.9, the bi-specific antibodies were then eluted. In this procedure, it is advantageous if the grain size of the carrier material to which the protein A is bonded is <50 µm. In comparison with carrier materials of 100 µm grain size substantially sharper elution peaks could be obtained in this way. The relatively high pH makes sure in this case that exclusively antibody variants with hetero-Fc ($CH_2$—$CH_3$/$CH_2'$—$CH_3'$) configuration were present in the elute. Since only one binding domain of the protein A molecule binds with the mouse based $CH_2$—$CH_3$ region in the bi-specific antibodies, a drop in the pH value from 7 to only 5.85 is sufficient for the redemption of the bi-specific antibodies. For the subsequent regeneration of the protein A, 0.1M Na-citrate buffer adjusted to a pH 3.5 is conducted through the column whereby also the bonded homo-Fc ($CH_2$—$CH_3$) 2 variants of immune origin are separated. The higher binding affinity of the parental mouse antibodies and the homo mouse Fc variants is based on the additional second interacting protein A binding domain. The purification procedure for the bi-specific antibodies by way of protein A is not shown in FIG. 2.

The purity of the bi-specific antibody (pH 5.85)—and the parental mouse antibody (pH 3.5)—fractions was examined by means of a mono S cation exchanger column (FIGS. 3 and 4) and also in the ELISA.

Figure 3:
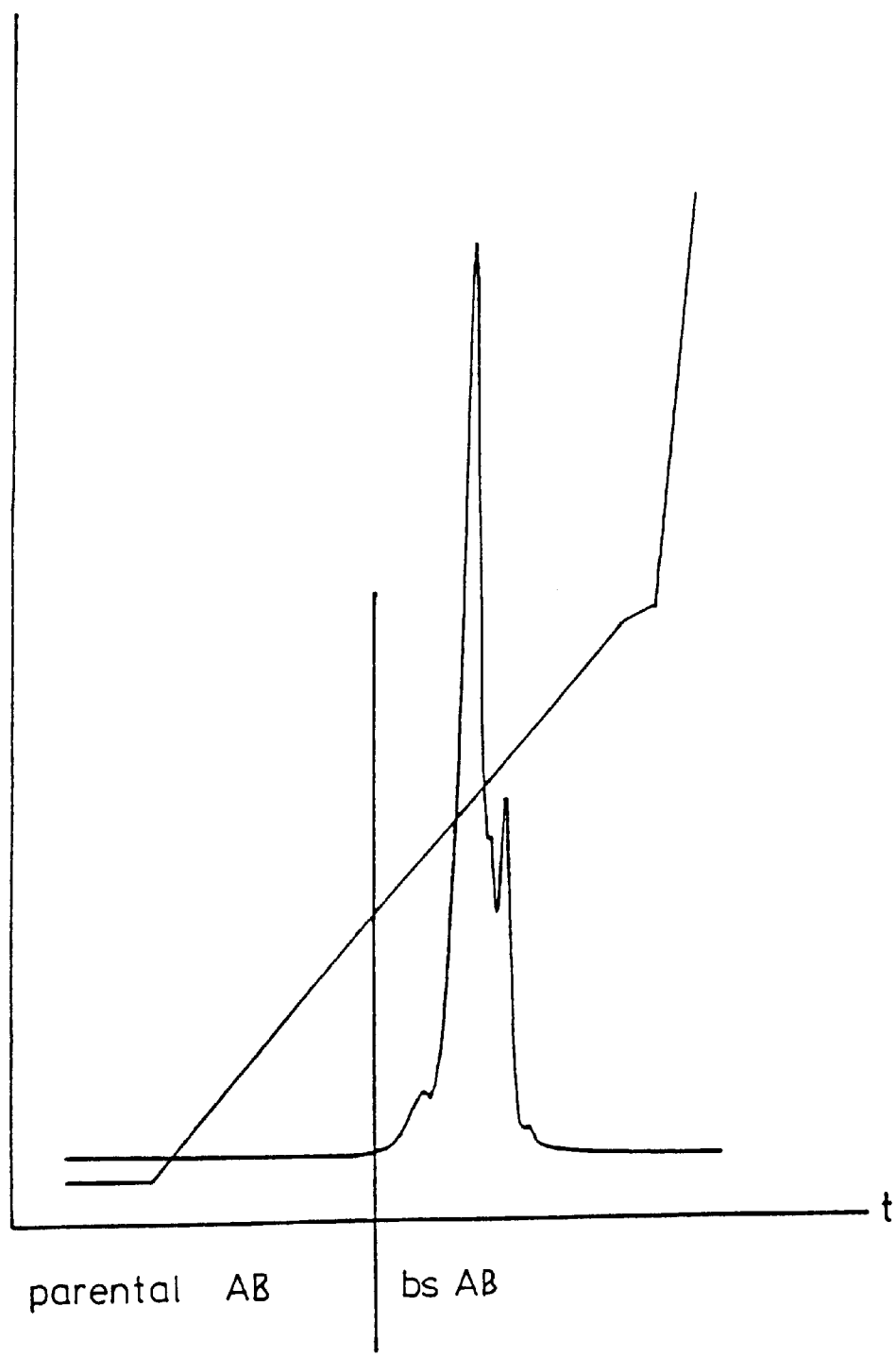
FIGS. 3 and 4 show the composition of the two peaks of FIG. 2.

With different glucosilation of the antibodies a peak which corresponds to a protein A elution fraction in the cation exchanger-chromatography is split into several peaks (see FIG. 3 wherein the pure bi-specific antibody peak according to example 1 is split into several peaks).

Figure 4:
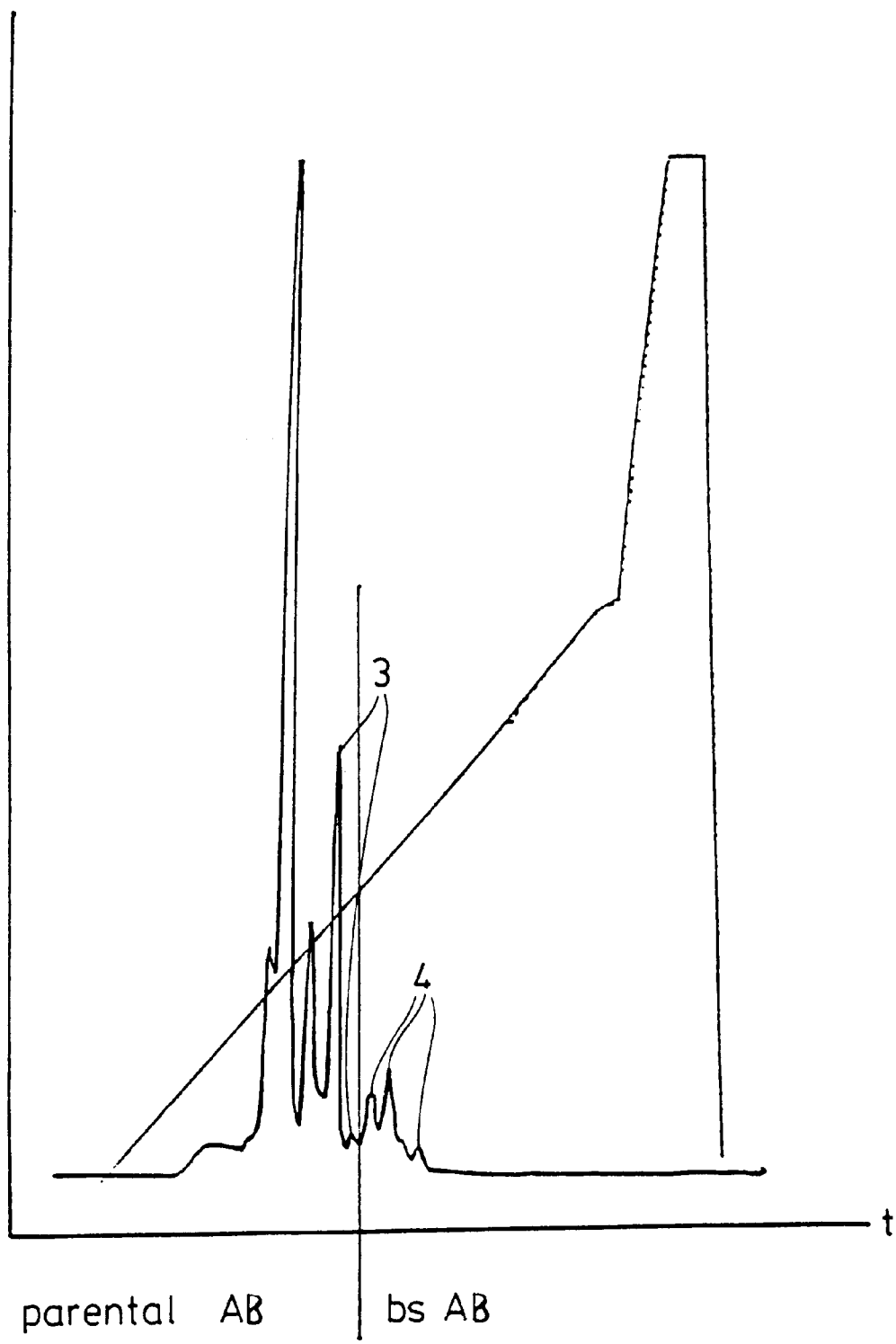

FIG. 4 shows the composition of the parental mouse antibodies. Mismatches are contained in the peaks 3. Bi-specific antibodies are contained in the peaks 4 as trace components. From this diagram, it is understood that mismatches are present in a substantially more limited manner than in mouse/mouse quadromas. For this reason, this modified quadroma method wherein different hybridomas are combined is particularly suitable for the manufacture of bi-specific antibodies.

Definition of the pH ranges

1. The redemption of the parental mouse IgG2a antibodies begins below a pH value of 5. The redemption of the bi-specific antibodies starts below a pH value of 6.8.

2. Above a pH value of 5.2, there is essentially no redemption of parental IgG2a mouse antibodies (<2%).

At a pH value of 6, there is a quantitative elution of the bi-specific antibodies after an extended presence of the elution buffer with low bi-specific antibody concentration.

3. Optimal range (pH 5.8±0.2) with short elution times and maximum bi-specific antibody concentration. It has been found that protein A on a large-grain carrier with a diameter >100 µm is less suitable for the redemption than protein A on a carriers <50 µm.

Comments regarding the cation exchanger chromatography: the operating condition for the mono S runs were identical. An NaCl-gradient of 50–800 mM was employed wherein the pH was maintained constant by means of 50 mM MES at a pH of 5.5.

Estimates of the amount ratios of the various antibody variants in the culture supernatant of the heterologous hybrid-hybridoma (G2):

To estimate, in percentages, the amount ratios of the particular antibody variants, first, the surface areas under the respective clearly defined peaks of the mono test runs were utilized and, second, the ELISA data of the particular peaks were taken into consideration. For the quadroma G2 an amount of 20–25% properly paired bi-specific antibodies could be determined with these methods which represents a 2.5 fold increase in the bi-specific antibody yield when compared with conventional mouse/mouse quadromas. Since a value of 33% for the bi-specific antibody fractions cannot be exceeded in the quadroma cells because of the free pairing of heavy mouse and rat Ig-chains, a yield of 20–25% is near the optimal yield.

EXAMPLE 2a

This example shows that the one-step purification of the bi-specific antibody component by way of protein A is possible even within a species. In this case, one of the participating initial antibodies must have a subclass which does not bind to protein A. In the present (actual) example the bi-specific antibody is composed of two humanized antibodies. In this case, the original in urine sequences of the $CH_2$—$CH_3$ domains were replaced in clone A by the human sequences of the subclass IgG1. In clone B, the original rat sequences of the $CH_2$—$CH_3$ domains were replaced by human sequences of the subclass IgG3. The human subclass IgG3 herein represents the part of the bi-specific antibodies which does not bind to protein A.

In principle, the human subclass IgG1 can be replaced in this example by any other human subclass that binds to protein A.

Figure 1:
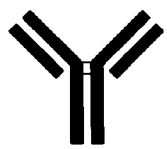
FIG. 1 shows all the antibody variants secerned from hybrid–hybridoma cells.
Figure 1:
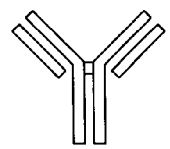
Figure 1:
Figure 1:
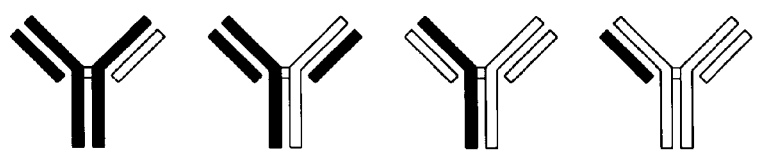
Figure 1:
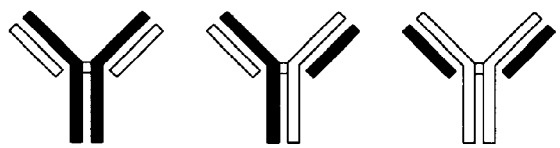

The purification of the bi-specific antibodies from the culture supernatant of such a quadroma may be performed essentially in accordance with the protocol as shown in FIG. 1.

EXAMPLE 2b

This variation of example 2a relates to bi-specific antibodies of two complete humanized antibodies of which one partner contains the $CH_2$—$CH_3$ region of the human subclass IgG3. If it is taken into consideration that the other human subclass which participates in the bi-specific antibody group binds with a protein A, the purification principle presented herein can also be applied to such human antibodies.

EXAMPLE 3

In example 3, it is shown that, by fusion of suitably initial clones, the advantage of the purification methods described herein can be combined with a desired monovalent binding of the bi-specific antibodies. In this particular case, a rat antibody with an interesting specificity could be fused with a mouse antibody with a specificity which is irrelevant in the respective in vitro- or invivo system. The parental bivalent rat antibody would again be separated already during charging of the protein A column because it is not bonded to protein A.

The greatest possible yield is guaranteed in this example also because of the preferential pairing of the heavy and light chains of the rat with one another. Another advantage of the variant described herein is the effect or function of the bi-specific antibody gained additionally by the mouse subclass IgG2a if the participating rat antibody is part of the subclass IgG2a or IgG1.

EXAMPLE 4

Example 4 concerns the combination of a monoclonal antibody which is directed against a human antigen with an antibody which is directed against a murine antigen. Such a bi-specific antibody could act as follows:

1. By suitable selection of the species or, respectively, subclasses of the participating monoclonal antibodies it could utilize the advantages of the present invention for the purification of bi-specific antibodies as well as an increased, correct passing of the heavy/light immunoglobulin chain with mouse/rat quadromas.

2. Based on the initially mentioned specificity in a human and, respectively, in a mouse, such a bi-specific antibody could bind only with one bond (monovalent), a property which is important for certain forms of therapy such as the depletion of certain lymphocyte populations.

3. By a suitable selection of subclasses of the participating antibodies such a bi-specific antibody could have certain effects or functions.

4. The bi-specific antibody could be tested preclinically for its biocompatibility in the mouse which would permit to draw conclusions with respect to the properties in humans.

EXAMPLE 5

Since Rousseaux [13] has shown in 1981 that the rat subclass IgG2c is the only rat subclass that binds to a protein A, bi-specific antibodies of rat/rat quadromas, wherein one of the fusion partners produces the rat subclass IgG2c, could also be purified in accordance with the protocol presented in FIG. 1. This would be at the same time the first purification method for bi-specific antibodies of the rat on the basis of protein A.

The following two pages include a listing of literature which is of interest in connectin with the present invention and to which reference is made in the body of the specification.

[1] Karawajew L., Micheel B., Behrsing O., Gaestel M. (1987) J.Immunol. Methods 96:265
[2] Nitta T., Sato K., Yagita H., Okumura K., Ishii S. (1990) Lancet 335:368
[3] MacLean J. A., Su Z., Guo Y., Sy M., Colvin R. B., Wong J. T. (1993) J.Immunol. 150:1619–1628
[4] Brennan M., Davison P. F., Paulus H. (1985) Preparation of bispecific antibodies by chemical recombination of monoclonal immunglobulin G1-fragments. Science 229:81
[5] Kostelny S. A., Cole M. S., Tso J. Y. (1992) J. Immunol. 148:1547–1553
[6] Clark M., Gilliland L., Waldmann H. (1988) Hybrid antibodies for therapy. Monoclonal antibody therapy. Prog Allergy. Basel, Karger, vol45:31–49
[7] De Lau W. B. M., Heije K., Neefjes J. J., Oosterwegel M., Rozemuller E., Bast B. J. E. G. (1991) Absence of preferential homologous H/L chain association in hybrid-hybridomas. J. Immunol.146:906–914
[8] Link B. K., Weiner G. J. (1993) Production and characterization of bispecific IgG capable of inducing T-cell mediated lysis of malignant B cells. Blood 81:3343–3349
[9] Ey P. L., Prowse S. J., Jenkin C. R. (1978) Isolation of pure IgG1, IgG2a and IgG2b immunoglobulins from mouse serum using protein A-Sepharose. Immunochemistry 15:429–436
[10] Couderc J., Kazatchkine M. D., Ventura M., Duc H. T., Maillet F., Thobie N., Liacopoulos P. (1985) Activation of the human classical complement pathway by a mouse monoclonal hybrid IgG1-2a monovalent anti-TNP antibody bound to TNP-conjugated cells. J. Immunol. 134:486–491
[11] Kuppen P. J. K. et al. (1993) The development and purification of a bispecific antibody for lymphokine-activated killer cell targeting against the rat colon carcinoma CC531. Cancer Immunol. Immunother. 36:403–408
[12] Deisenhofer J. (1981) Crystallographic refinement and atomic models of a human Fc fragment and its complex with fragment B of protein A from Staphylococcus aureus at 2.9 and 2.8 A resolution. Biochemistry 20:2361–2370
[13] Rousseaux J., Rousseaux-Prevost R., Bazin H., Biserte G. (1981) Tryptic cleavage of rat IgG: a comperative study between subclasses. Immunol. Lett. 3:93

What is claimed is:

1. A method for making heterologous bi-specific antibodies comprising the steps of:
    a) providing a quadroma fused from hybridomas of which one produces first antibodies which have an affinity to the binding domain of protein A wherein said first antibodies are mouse antibodies, human or humanized antibodies of the subclass IgG1, IgG2, IgG4 or rat antibodies of the subclass IgG2c and the other hybridoma produces second antibodies which, in comparison with the first antibodies, have a smaller or no affinity to the binding domain of protein A, the second antibodies being rat antibodies of the subclass IgG1, IgG2a, IgG2b, IgG3 or human or humanized antibodies of the subclass IgG3,
    b) multiplying and cultivating the quadromas in a culture,
    c) applying the quadroma culture supernatant to a column which is coated with a material having a grain size less than 50 μm which contains binding domains of protein A as functional groups, d) washing out in the respective pH range the antibodies which are not bonded, and, e) subjecting the bi-specific antibodies to elution in a pH range of 5.6 to 6.0 which is at least 0.5 units above the pH at which the antibodies with greater affinity to the binding domain of protein A are still bonded.

2. A method for making heterologous bi-specific antibodies according to claim 1, wherein said mouse antibodies and antibodies of the subclass IgG2a, IgG2b or IgG4.

3. A heterologous bi-specific antibody made in accordance with claim 1 so as to comprise a mouse antibody of the subclass IgG2a fused with a rat antibody of the subclass IgG2b.

4. A heterologous bi-specific antibody made in accordance with claim 1, so as to comprise a human or humanized antibody of the subclass IgG1 fused with a human or humanized antibody of the subclass IgG3.

5. A heterologous bi-specific antibody made in accordance with claim 1, so as to comprise a rat antibody of the subclass IgG2c fused with a rat antibody of the subclass IgG2b.

6. A heterologous bi-specific antibody made in accordance with claim 1, so as to comprise a human or humanized antibody of the subclass IgG1 fused with a rat antibody of the subclass IgG1, IgG2a, IgG2b or IgG3.

7. A heterologous bi-specific antibody made in accordance with claim 1, so as to comprise a rat antibody of the subclass IgG2c fused with a human or humanized antibody of the subclass IgG3.

8. A heterologous bi-specific antibody made in accordance with claim 1, so as to comprise a mouse antibody of the subclass IgG2a, IgG2b, or IgG4 fused with a human or humanized antibody of the subclass IgG3.

* * * * *